(12) United States Patent
Fack et al.

(10) Patent No.: US 7,151,079 B2
(45) Date of Patent: Dec. 19, 2006

(54) COSMETIC COMPOSITIONS CONTAINING A FRUCTAN, A POLYSACCHARIDE AND A BENEFICIAL AGENT, AND USES THEREOF

(75) Inventors: Géraldine Fack, Levallois-Perret (FR); Chrystel Pourille-Grethen, Clichy (FR); Serge Restle, Saint-Prix (FR)

(73) Assignee: L'Oreal (FR)

( * ) Notice: Subject to any disclaimer, the term of this patent is extended or adjusted under 35 U.S.C. 154(b) by 189 days.

(21) Appl. No.: 10/250,896

(22) PCT Filed: Jan. 11, 2002

(86) PCT No.: PCT/FR02/00105

§ 371 (c)(1),
(2), (4) Date: Dec. 29, 2003

(87) PCT Pub. No.: WO02/055034

PCT Pub. Date: Jul. 18, 2002

(65) Prior Publication Data

US 2004/0106529 A1 Jun. 3, 2004

(30) Foreign Application Priority Data

Jan. 12, 2001 (FR) .................. 01 00408

(51) Int. Cl.
*C11D 3/22* (2006.01)

(52) U.S. Cl. .............. 510/121; 510/119; 510/122; 510/130; 510/131; 510/151; 510/470; 510/471; 510/473; 510/474

(58) Field of Classification Search ............. 510/119, 510/121, 122, 470, 471, 130, 131, 151, 473, 510/474
See application file for complete search history.

(56) References Cited

U.S. PATENT DOCUMENTS

| 4,017,460 A | 4/1977 | Tessler |
| 5,243,072 A | 9/1993 | Gruning et al. |
| 5,455,340 A | 10/1995 | Bernard et al. |
| 5,520,200 A * | 5/1996 | Sturla .................. 132/206 |
| 5,700,455 A * | 12/1997 | Hinterwaldner et al. . 424/70.14 |
| 5,871,756 A | 2/1999 | Jeffcoat et al. |
| 5,877,144 A | 3/1999 | Ehrhardt et al. |
| 6,025,006 A * | 2/2000 | Miller et al. ............ 426/564 |
| 6,033,710 A * | 3/2000 | Miller et al. ............ 426/564 |
| 6,261,578 B1 * | 7/2001 | Dupuis .................. 424/401 |
| 6,451,300 B1 * | 9/2002 | Dunlop et al. .......... 424/70.27 |
| 6,468,988 B1 * | 10/2002 | Mann .................... 514/58 |
| 6,685,952 B1 * | 2/2004 | Ma et al. ................ 424/401 |

FOREIGN PATENT DOCUMENTS

| AU | 746456 | 7/2001 |
| DE | 3833658 | 4/1990 |
| DE | 100 04 644 A | 8/2001 |
| EP | 0 689 829 | 1/1996 |
| EP | 0 792 888 A | 9/1997 |
| EP | 0 797 979 | 10/1997 |
| EP | 0 950 393 | 10/1999 |
| EP | 1 174 118 A | 1/2002 |
| FR | 2 795 953 A | 1/2001 |
| FR | 2 795 954 A | 1/2001 |
| JP | 7-304801 | 7/2000 |
| WO | WO-90/03779 | 4/1990 |
| WO | WO-96/22073 | 7/1996 |
| WO | WO-98/14482 A | 4/1998 |

OTHER PUBLICATIONS

Cottrell, et al. "Novel Polysaccharide Derivatives for Personal Care," National Starch and Chemical, ICI Group, Bridgewater, NJ 08807 (Sep. 8, 1998).

* cited by examiner

*Primary Examiner*—Charles Boyer
(74) *Attorney, Agent, or Firm*—Lerner, David, Littenberg, Krumholz & Mentlik, LLP

(57) ABSTRACT

The invention relates to novel cosmetic compositions comprising, in a cosmetically acceptable medium, at least one fructan, at least one polysaccharide and at least one beneficial agent, a combination which gives the cosmetic compositions a velvety-smooth texture. Said composition can be easily rinsed off. Hair treated with said composition feels soft and contains no residue. The compositions are particularly suitable for washing and/or conditioning keratinous matter, such as the hair and skin.

49 Claims, No Drawings

COSMETIC COMPOSITIONS CONTAINING A FRUCTAN, A POLYSACCHARIDE AND A BENEFICIAL AGENT, AND USES THEREOF

The present invention relates to novel cosmetic compositions comprising, in a cosmetically acceptable medium, at least one fructan, at least one polysaccharide and at least one beneficial agent.

It is well known that hair which has been sensitized (i.e. damaged and/or embrittled) to varying extents under the action of atmospheric agents or under the action of mechanical or chemical treatments, such as dyeings, bleachings and/or permanent waves, is often difficult to disentangle and style, and lacks softness.

Combinations of polymers with thickening natures have already been provided for the treatment of keratinous substances and in particular the hair. The combinations which have been disclosed include combinations of polysaccharides, such as inulin, and of acrylic terpolymers comprising a urethane unit.

However, such combinations have disadvantages, such as problems of rinsability, problems of stability at acidic pH, difficulties of distribution over keratinous substances, and inadequate cosmetic properties.

The Applicant Company has now discovered that the combination of a fructan with polysaccharides and beneficial agents makes it possible to overcome these disadvantages.

Thus, following much research directed at the question, it has now been found by the Applicant Company that, by introducing a fructan and a polysaccharide into the compositions, in particular hair compositions, of the prior art based on beneficial agents, it is possible to limit, indeed even eliminate, the problems generally related to the use of such compositions.

Furthermore, this combination introduces a melting texture to the cosmetic compositions, that is to say which disappears rapidly into the scalp. The hair treated with this composition has a soft and residue-free feel.

Furthermore, the compositions of the invention, applied to the skin in particular in the form of a foam bath or shower gel, improve the softness of the skin.

Fructans are prepared from natural products and thus exhibit the advantage of being biodegradable. In combination with beneficial agents for keratinous substances, they make it possible to improve the performance of cosmetic treatment compositions in comparison with the combinations formed of cationic starches and of beneficial agents for keratinous substances of the prior art.

Thus, according to the present invention, provision is now made for novel cosmetic compositions comprising, in a cosmetically acceptable medium, at least one fructan, at least one polysaccharide and at least one beneficial-agent.

Another subject matter of the invention relates to the use of a fructan and of a polysaccharide in or for the manufacture of a cosmetic composition comprising a beneficial agent.

The various subject matters of the invention will now be described in detail. All the meanings and definitions of the compounds used in the present invention given below are valid for all the subject matters of the invention.

The term "beneficial agent for keratinous substances" is used to describe an agent capable in particular of protecting, beautifying, conditioning, treating and/or retaining the form of keratinous substances and in particular the hair.

Fructans or fructosans are oligosaccharides or polysaccharides comprising a sequence of anhydrofructose units optionally combined with one [lacuna] more different saccharide residues of the fructose. Fructans can be linear or branched. Fructans can be products obtained directly from a plant or microbial source or else products with a chain length which has been modified (increased or reduced) by splitting, synthesis or hydrolysis, in particular of the enzymatic variety. Fructans generally have a degree of polymerization from 2 to approximately 1 000 and preferably from 3 to approximately 60.

Three groups of fructans are distinguished. The first group corresponds to products with fructose units which are mostly bonded via $\beta$-2-1 bonds. These are essentially linear fructans, such as inulins.

The second group also corresponds to linear fructoses but the fructose units are essentially bonded via $\beta$-2-6 bonds. These products are levans.

The third group corresponds to mixed fructans, that is to say fructans having $\beta$-2-6 and $\beta$-2-1 sequences. These are essentially branched fructans, such as graminans.

The preferred fructans are inulins. Inulin can be obtained, for example, from chicory, the dahlia or Jerusalem artichokes.

The fructan is preferably used in an amount of between 0.01 and 20% by weight with respect to the total weight of the composition. More preferably, this amount is between 0.05 and 15% by weight with respect to the total weight of the composition and more preferably still between 0.1 and 10% by weight.

The polysaccharides other than the fructans is generally thickening and chosen in particular from glucans, modified or unmodified starches (such as those resulting, for example, from cereals, such as wheat, corn or rice, from vegetables, such as yellow split peas, or from tubers, such as potatoes or manioc), amylose, amylopectin, glycogen, dextrans, celluloses and their derivatives (methylcelluloses, hydroxyalkylcelluloses, ethylhydroxyethylcelluloses or carboxy-methylcelluloses), mannans, xylans, lignins, arabans, galactans, galacturonans, chitin, chitosans, glucoronoxylans, arabinoxylans, xyloglucans, glucomannans, pectic acids and pectins, alginic acid and alginates, arabinogalactans, carrageenins, agars, glycosaminoglucans, gums arabic, gums tragacanth, ghatti gums, karaya gums, locust bean gums, galactomannans, such as guar gums and their nonionic derivatives (hydroxypropyl guar), and xanthan gums, and their mixtures.

Generally, the compounds of this type which can be used in the present invention are chosen from those which are described in particular in "Encyclopedia of Chemical Technology, Kirk-Othmer, Third Edition, 1982, volume 3, pp. 896–900, and volume 15, pp. 439–458", in "Polymers in Nature, by E. A. MacGregor and C. T. Greenwood, published by John Wiley & Sons, Chapter 6, pp. 240–328, 1980" and in Industrial Gums—Polysaccharides and their Derivatives, edited by Roy L. Whistler, Second Edition, published by Academic Press Inc.", the content of these three works being entirely included in the present application by way of reference.

Use will preferably be made of pectins, starches, guar gums, or celluloses and their derivatives.

The polysaccharide is present at a concentration of between 0.01% and 20% by weight with respect to the total weight of the composition, preferably between 0.05% and 10% by weight.

The beneficial agents for keratinous substances can be chosen from:

(1) amino acids, oligopeptides, peptides or proteins, which may or may not be hydrolyzed and which may or may not be modified,
(2) branched or unbranched fatty acids and alcohols,
(3) animal, vegetable or mineral waxes,
(4) ceramides and pseudoceramides,
(5) hydroxylated organic acids,
(6) UV screening agents,
(7) antioxidants and agents for combating free radicals,
(8) chelating agents,
(9) antidandruff agents,
(10) seborrhea-regulating agents,
(11) soothing agents,
(12) cationic surfactants,
(13) amphoteric polymers,
(14) organomodified or non-organomodified silicones,
(15) mineral, vegetable or animal oils,
(16) polyisobutenes and poly(α-olefins),
(17) esters,
(18) soluble or dispersed anionic polymers,
(19) soluble or dispersed nonionic polymers, and their mixtures.

The composition according to the invention can comprise one or more amino acids, oligopeptides, peptides or proteins, which may or may not be hydrolyzed and which may or may not be modified. Mention may be made, as amino acids, of, for example, cysteine, lysine, alanine, N-phenylalanine, arginine, glycine, leucine, and their mixtures. Mention may in particular be made, as oligopeptides, peptides or proteins, which may or may not be hydrolyzed and which may or may not be modified, which can be used in the composition according to the invention, of hydrolysates of wool or silk proteins, which may or may not be modified, or plant proteins, such as wheat proteins.

The composition according to the invention can comprise one or more branched or unbranched fatty acids and alcohols. Mention may in particular be made, among fatty acids suitable in the present invention, of $C_8$–$C_{30}$ carboxylic acids, such as palmitic acid, oleic acid, linoleic acid, myristic acid, stearic acid, lauric acid, and their mixtures. The fatty alcohols which can be used in the present invention comprise in particular $C_8$–$C_{30}$ alcohols, such as, for example, palmityl, oleyl, linoleyl, myristyl, stearyl and lauryl alcohols, and their mixtures.

The composition according to the invention can comprise one or more animal, vegetable or mineral waxes.

A wax within the meaning of the present invention is a lipophilic compound, solid at ambient temperature (approximately 25° C.), with a reversible solid/liquid change of state, having a melting point of greater than approximately 40° C. and which can range up to 200° C., and exhibiting, in the solid state, an anisotropic crystalline arrangement. Generally, the size of the crystals of the wax is such that the crystals diffract and/or scatter light, conferring on the composition which comprises them a cloudy appearance which is more or less opaque. On bringing the wax to its melting point, it is possible to render it miscible with oils and to form a microscopically homogeneous mixture but, on bringing the temperature of the mixture back to ambient temperature, a recrystallization of the wax from the oils of the mixture is obtained which is detectable microscopically and macroscopically (opalescence).

Mention may be made, as waxes which can be used in the present invention, of waxes of animal origin, such as beeswax, spermaceti, lanolin wax and lanolin derivatives; vegetable waxes, such as carnauba wax, candelilla wax, ouricury wax, Japan wax, cocoa butter or cork fiber or sugarcane waxes; mineral waxes, for example paraffin wax, petrolatum wax, lignite wax or microcrystalline waxes or ozokerites, and their mixtures.

The composition according to the invention can comprise one or more ceramides and/or pseudoceramides. Mention may in particular be made of ceramides of the classes I, II, III and V according to the Dawning classification, and their mixtures.

Such compounds are, for example:
2-(N-linoleoylamino)octadecane-1,3-diol,
2-(N-oleoylamino)octadecane-1,3-diol,
2-(N-palmitoylamino)octadecane-1,3-diol,
2-(N-stearoylamino)octadecane-1,3-diol,
2-(N-behenoylamino)octadecane-1,3-diol,
2-(N-[2-hydroxypalmitoyl]amino)octadecane-1,3-diol,
2-(N-stearoylamino)octadecane-1,3,4-triol and in particular N-stearoylphytosphingosine,
2-(N-palmitoylamino)hexadecane-1,3-diol, or the mixtures of these compounds.

Use may also be made of specific mixtures, such as, for example, mixtures of ceramide(s) 2 and of ceramide(s) 5 according to the Downing classification.

Use may also be made of the compounds of formula (I) for which $R_1$ denotes a saturated or unsaturated alkyl radical derived from $C_{12}$–$C_{22}$ fatty acids; $R_2$ denotes a galactosyl or sulfogalactosyl radical; and $R_3$ denotes a saturated or unsaturated $C_{12}$–$C_{22}$ hydrocarbonaceous radical and preferably a —CH=CH—(CH$_2$)$_{12}$—CH$_3$ group.

Mention may be made, by way of example, of the product composed of a mixture of glycoceramides sold under the trade name Glycocer by Waitaki International Biosciences.

Use may also be made of the compounds of formula (I) disclosed in patent applications EP-A-0 227 994, EP-A-0 647 617, EP-A-0 736 522 and WO 94/07844.

Such compounds are, for example, Questamide H (bis(N-hydroxyethyl-N-cetyl)malonamide), sold by Quest, or the N-(2-hydroxyethyl)-N-(3-cetyloxy-2-hydroxy-propyl) amide of cetylic acid.

Use may also be made of N-docosanoyl-N-methyl-D-glucamine, disclosed in patent application WO 94/24097.

The composition according to the invention can comprise one or more hydroxylated organic acids chosen from those well known and used in the art. Mention may in particular be made of citric acid, lactic acid, tartaric acid, malic acid, and their mixtures.

The composition according to the invention can comprise one or more sunscreens active in the UV-A and/or UV-B regions well known to a person skilled in the art. Mention may in particular be made of dibenzoylmethane derivatives, such as 4-methyldibenzoylmethane, 4-isopropyldibenzoylmethane, 4-tert-butyldibenzoylmethane, 2,4-dimethyldibenzoylmethane or 4-tert-butyl-4'-diisopropyldibenzoylmethane, p-aminobenzoic acid and its esters, such as 2-ethylhexyl p-dimethylaminobenzoate and N-propoxylated ethyl p-aminobenzoate, salicylates, such as triethanolamine salicylate, cinnamic acid esters, such as 2-ethylhexyl 4-methoxycinnamate or methyl diisopropylcinnamate, menthyl anthranilate, benzotriazole derivatives, triazine derivatives, β,β'-diphenylacrylate derivatives, such as 2-ethylhexyl 2-cyano-3,3-diphenylacrylate and ethyl 2-cyano-3,3-diphenylacrylate, 2-phenylbenzimidazole-5-sulfonic acid and its salts, benzophenone derivatives, benzylidenecamphor derivatives, silicone-comprising screening agents, and the like, and their mixtures.

Mention may be made, as antioxidants and agents for combating free radicals which can be used in the present invention, of, for example, ascorbic acid, ascorbylated compounds, such as ascorbyl dipalmitate, t-butylhydroquinone, polyphenols, such as phloroglucinol, sodium sulfite, erythorbic acid, flavonoids, and their mixtures.

The composition according to the invention can comprise one or more chelating agents chosen in particular from EDTA (ethylenediaminetetraacetic acid) and its salts, such as disodium EDTA and dipotassium EDTA, phosphate-comprising compounds, such as sodium metaphosphate, sodium hexametaphosphate or tetrapotassium pyrophosphate, phosphonic acids and their salts, such as the salts of ethylenediaminetetra-methylenephosphonic acid, and their mixtures.

The composition according to the invention can comprise one or more antidandruff agents chosen, for example, from:
benzethonium chloride, benzalkonium chloride, chlorhexidine, chloramine-T, chloramine-B, 1,3-dibromo-5,5-dimethylhydantoin, 1,3-dichloro-5,5-dimethyl-hydantoin, 3-bromo-1-chloro-5,5-dimethylhydantoin or N-chlorosuccinimide;
1-hydroxy-2-pyridone derivatives, such as, for example, 1-hydroxy-4-methyl-2-pyridone, 1-hydroxy-6-methyl-2-pyridone and 1-hydroxy-4,6-dimethyl-2-pyridone;
trihalocarbamides;
triclosan;
azole-comprising compounds, such as climbazole, ketoconazole, clotrinazole, econazole, isoconazole and miconazole b;
antifungal polymers, such as amphotericin B or nystatin;
selenium sulfides;
sulfur in its various forms, cadmium sulfide, allantoin, coal or wood tars and their derivatives, in particular oil of cade, undecylenic acid, fumaric acid, or allylamines, such as terbinafine;
or a mixture of these antidandruff agents.

They may also be used in the form of their addition salts with physiologically acceptable acids, in particular in the form of salts of sulfuric, nitric, thiocyanic, hydrochloric, hydrobromic, hydriodic, phosphoric, acetic, benzoic, glycolic, aceturic, succinic, nicotinic, tartaric, maleic, palmitic, methanesulfonic, propanoic, 2-oxopropanoic, propanedioic, 2-hydroxy-1,4-butanedioic, 3-phenyl-2-propenoic, α-hydroxybenzeneacetic, ethanesulfonic, 2-hydroxyethanesulfonic, 4-methylbenzenesulfonic, 4-amino-2-hydroxybenzoic, 2-phenoxybenzoic, 2-acetyloxybenzoic, picric, lactic, citric, malic and oxalic acids and of amino acids.

The antidandruff agents mentioned above can also, if appropriate, be used in the form of their addition salts with physiologically acceptable organic or inorganic bases. Examples of organic bases are in particular alkanolamines with low molecular weights, such as ethanolamine, diethanolamine, N-ethyl-ethanolamine, triethanolamine, diethylaminoethanol or 2-amino-2-methylpropanedione; nonvolatile bases, such as ethylenediamine, hexamethylenediamine, cyclohexylamine, benzylamine or N-methylpiperazine; quaternary ammonium hydroxides, for example trimethylbenzyl hydroxide; or guanidine and its derivatives, and particularly its alkylated derivatives. Examples of inorganic bases are in particular the salts of alkali metals, such as sodium or potassium; ammonium salts; the salts of alkaline earth metals, such as magnesium or calcium; or the salts of cationic di-, tri- or tetravalent metals, such as zinc, aluminum and zirconium. Alkanolamines, ethylenediamine and inorganic bases, such as the salts of alkali metals, are preferred.

The composition according to the invention can comprise one or more seborrhea-regulating agents, such as succinyl-chitosan and poly-β-alanine, and their mixtures.

The composition according to the invention can comprise one or more soothing agents, such as azulene and glycyrrhetinic acid, and their mixtures.

The composition according to the invention can comprise one or more cationic surfactants well known per se, such as salts of primary, secondary or tertiary fatty amines which are optionally polyoxyalkylenated; quaternary ammonium salts, such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides with a cationic nature.

The composition according to the invention can comprise one or more amphoteric polymers.

The amphoteric polymers which can be used in accordance with the invention can be chosen from polymers comprising B and C units distributed randomly in the polymer chain, where B denotes a unit deriving from a monomer comprising at least one basic nitrogen atom and C denotes a unit deriving from an acidic monomer comprising one or more carboxyl or sulfo groups or else B and C can denote groups deriving from zwitterionic carboxybetaine or sulfobetaine monomers; B and C can also denote a cationic polymer chain comprising primary, secondary, tertiary or quaternary amine groups, in which at least one of the amine groups carries a carboxyl or sulfo group connected via a hydrocarbonaceous group, or else B and C form part of a chain of a polymer comprising an ...-dicarboxyethylene unit, one of the carboxyl groups of which has been reacted with a polyamine comprising one or more primary or secondary amine groups.

The amphoteric polymers corresponding to the definition given above which are more particularly preferred are chosen from the following polymers:

(1) polymers resulting from the copolymerization of a monomer derived from a vinyl compound carrying a carboxyl group, such as more particularly acrylic acid, methacrylic acid, maleic acid or α-chloroacrylic acid, and of a basic monomer derived from a substituted vinyl compound comprising at least one basic atom, such as more particularly dialkylaminoalkyl methacrylate and acrylate or dialkylaminoalkylmethacrylamide and -acrylamide. Such compounds are disclosed in U.S. Pat. No. 3,836,537. Mention may also be made of the sodium acrylate/acrylamidopropyltrimethyl-ammonium chloride copolymer sold under the name Polyquart® KE 3033 by Henkel.

The vinyl compound can also be a dialkyldiallylammonium salt, such as diethyldiallyl-ammonium chloride.

Copolymers of acrylic acid and of the latter monomer are provided under the names Merquat® 280, Merquat® 295 and Merquat® Plus 3330 by Calgon.

(2) polymers comprising units deriving:
a) from at least one monomer chosen from acrylamides or methacrylamides substituted on the nitrogen by an alkyl group,
b) from at least one acidic comonomer comprising one or more reactive carboxyl groups, and
c) from at least one basic comonomer, such as esters comprising primary, secondary, tertiary and quaternary amine substituents of acrylic and methacrylic acids and the quaternization product of dimethylaminoethyl methacrylate with dimethyl or diethyl sulfate.

The more particularly preferred N-substituted acrylamides or methacrylamides according to the invention are the groups in which the alkyl groups comprise from 2 to 12 carbon atoms and more particularly N-ethylacrylamide, N-tert-butylacrylamide, N-tert-octylacrylamide, N-octylacrylamide, N-decylacrylamide or N-dodecylacrylamide, and the corresponding methacrylamides.

The acidic comonomers are more particularly chosen from acrylic, methacrylic, crotonic, itaconic, maleic or fumaric acids and alkyl monoesters having 1 to 4 carbon atoms of maleic or fumaric acids or anhydrides. The preferred basic comonomers are aminoethyl, butylaminoethyl, N,N'-dimethylaminoethyl or N-tert-butylaminoethyl methacrylates. Use is particularly made of the copolymers for which the CTFA name (4th Ed., 1991) is octylacrylamide/-acrylates/butylaminoethyl methacrylate copolymer, such as the products sold under the name Amphomer® or Lovocryl® 47 by National Starch.

(3) partially or completely alkylated and crosslinked polyaminoamides deriving from polyaminoamides of general formula:

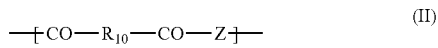

in which $R_{10}$ represents a divalent group derived from a saturated dicarboxylic acid, from an aliphatic mono- or dicarboxylic acid comprising an ethylenic double bond, from an ester of a lower alkanol having 1 to 6 carbon atoms of these acids, or from a group deriving from the addition of any one of said acids with a bisprimary or bis(secondary derived) amine, and Z denotes a group of a bisprimary, mono- or bissecondary polyalkylenepolyamine and preferably represents:

a) in the proportions of 60 to 100 mol %, the group

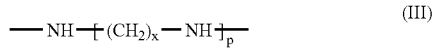

where x=2 and p=2 or 3, or else x=3 and p=2 this group deriving from diethylenetriamine, triethylenetetraamine or dipropylenetriamine;

b) in the proportions of 0 to 40 mol %, the above group (III), in which x=2 and p=1 and which derives from ethylenediamine, or the group deriving from piperazine:

c) in the proportions of 0 to 20 mol %, the group —NH—$(CH_2)_6$—NH— deriving from hexamethylenediamine, these polyaminoamines being crosslinked by addition of a bifunctional crosslinking agent chosen from epihalohydrins, diepoxides, dianhydrides or bisunsaturated derivatives, by means of 0.025 to 0.35 mol of crosslinking agent per amine group of the polyaminoamide, and alkylated by reaction with acrylic acid, chloracetic acid or an alkanesultone or their salts.

The saturated carboxylic acids are preferably chosen from acids having 6 to 10 carbon atoms, such as adipic, 2,2,4-trimethyladipic and 2,4,4-trimethyl-adipic, and terephthalic acids, and the acids comprising an ethylenic double bond, such as, for example, acrylic, methacrylic and itaconic acids.

The alkanesultones used in the alkylation are preferably propane- or butanesultone and the salts of the alkylating agents are preferably the sodium or potassium salts.

(4) polymers comprising zwitterionic units of formula:

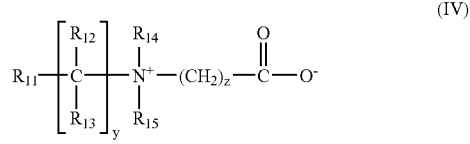

in which $R_{11}$ denotes a polymerizable unsaturated group, such as an acrylate, methacrylate, acrylamide or methacrylamide group, y and z each represent an integer from 1 to 3, $R_{12}$ and $R_{13}$ represent a hydrogen atom or a methyl, ethyl or propyl group, and $R_{14}$ and $R_{15}$ represent a hydrogen atom or an alkyl group such that the sum of the carbon atoms in $R_{14}$ and $R_{15}$ does not exceed 10.

The polymers comprising such units can also comprise units derived from nonzwitterionic monomers, such as dimethyl- or diethylaminoethyl acrylate or methacrylate or alkyl acrylates or methacrylates, acrylamides or methacrylamides, or vinyl acetate.

Mention may be made, by way of example, of the copolymer of methyl methacrylate and of methyl dimethylcarboxymethylammonioethyl methacrylate, such as the product sold under the name Diaformer® Z301 by Sandoz.

(5) polymers derived from chitosan comprising monomer units corresponding to the following formulae:

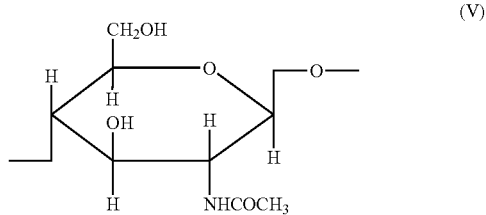

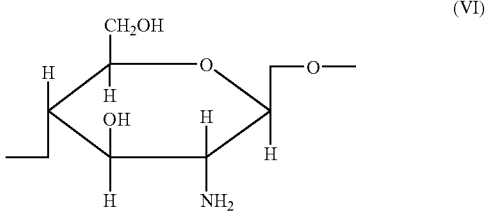

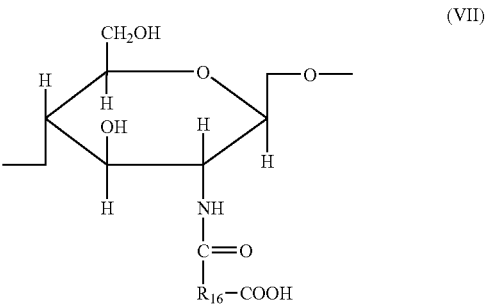

the unit (V) being present in proportions of between 0 and 30%, the unit (VI) in proportions of between 5 and 50% and the unit (VII) in proportions of between 30 and 90%, it being understood that, in this unit F, $R_{16}$ represents a group of formula:

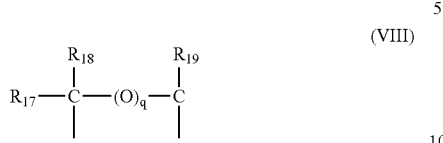

(VIII)

in which, if $q=0$, $R_{17}$, $R_{18}$ and $R_{19}$, which are identical or different, each represent a hydrogen atom, a methyl, hydroxyl, acetoxy or amino residue, a monoalkylamine residue or a dialkylamine residue, optionally interrupted by one or more nitrogen atoms and/or optionally substituted by one or more amine, hydroxyl, carboxyl, alkylthio or sulfo groups, or an alkylthio residue in which the alkyl group carries an amino residue, at least one of the $R_{17}$, $R_{18}$ and $R_{19}$ groups being, in this case, a hydrogen atom;

or, if $q=1$, $R_{17}$, $R_{18}$ and $R_{19}$ each represent a hydrogen atom, and the salts formed by these compounds with bases or acids.

(6) polymers derived from the N-carboxyalkylation of chitosan, such as the N-(carboxymethyl)chitosan or the N-(carboxybutyl)chitosan sold under the name Evalsan® by Jan Dekker.

(7) polymers corresponding to the general formula (IX) disclosed, for example, in French patent 1 400 366:

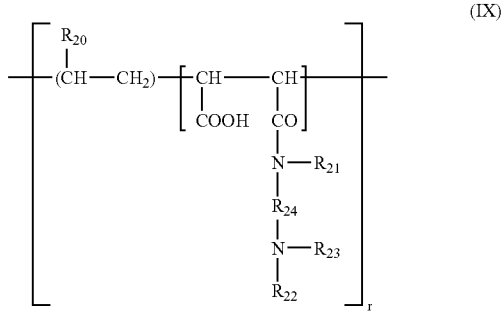

(IX)

in which $R_{20}$ represents a hydrogen atom or a $CH_3O$, $CH_3CH_2O$ or phenyl group, $R_{21}$ denotes hydrogen or a lower alkyl group, such as methyl or ethyl, $R_{22}$ denotes hydrogen or a lower alkyl group, such as methyl or ethyl, and $R_{23}$ denotes a lower alkyl group, such as methyl or ethyl, or a group corresponding to the formula: $-R_{24}-N(R_{22})_2$, $R_{24}$ representing a $-CH_2-CH_2-$, $-CH_2-CH_2-CH_2-$ or $-CH_2-CH(CH_3)-$ group and $R_{22}$ having the meanings mentioned above, as well as the higher homologs of these groups comprising up to 6 carbon atoms.

(8) amphoteric polymers of the -D-X-D-X- type chosen from:

a) polymers obtained by reaction of chloroacetic acid or sodium chloroacetate with compounds comprising at least one unit of formula:

-D-X-D-X-D- (X)

where D denotes a group

and X denotes the symbol E or E', E or E', which are identical or different, denote a bivalent group which is a straight- or branched-chain alkylene group comprising up to 7 carbon atoms in the main chain which is unsubstituted or substituted by hydroxyl groups and which can additionally comprise oxygen, nitrogen or sulfur atoms or 1 to 3 aromatic and/or heterocyclic rings; the oxygen, nitrogen and sulfur atoms being present in the form of ether, thioether, sulfoxide, sulfone, sulfonium, alkylamine or alkenylamine groups or hydroxyl, benzylamine, amine oxide, quaternary ammonium, amide, imide, alcohol, ester and/or urethane groups.

b) polymers of formula:

-D-X-D-X- (XI)

where D denotes a group

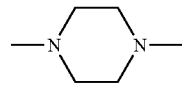

and X denotes the symbol E or E' and E' at least once, E having the meaning indicated above and E' is a bivalent group which is a straight- or branched-chain alkylene group having up to 7 carbon atoms in the main chain which is unsubstituted or substituted by one or more hydroxyl groups and which comprises one or more nitrogen atoms, the nitrogen atom being substituted by an alkyl chain optionally interrupted by an oxygen atom and necessarily comprising one or more carboxyl functional groups or one or more hydroxyl functional groups and betainized by reaction with chloroacetic acid or sodium chloroacetate.

(9) $(C_1-C_5)$alkyl vinyl ether/maleic anhydride copolymers partially modified by semiamidation with an N,N-dialkylaminoalkylamine, such as N,N-dimethylamino-propylamine, or by semiesterification with an N,N-dialkanolamine. These copolymers can also comprise other vinyl comonomers, such as vinylcaprolactam.

The particularly preferred amphoteric polymers according to the invention are those of the family (1).

The silicones which can be used in accordance with the invention can be soluble or insoluble in the composition and they can in particular be polyorganosiloxanes which are insoluble in the composition of the invention; they can be provided in the form of oils, of waxes, of resins or of gums.

Organopolysiloxanes are defined in more detail in the work by Walter Noll, "Chemistry and Technology of Silicones" (1968), Academic Press. They can be volatile or nonvolatile.

When they are volatile, the silicones are more particularly chosen from those having a boiling point of between 60° C. and 260° C. and more particularly still from:

(i) cyclic silicones comprising from 3 to 7 silicon atoms and preferably 4 to 5. They are, for example, octamethylcyclotetrasiloxane, sold in particular under the name of "Volatile Silicone 7202" by Union Carbide or "Silbione 70045 V 2" by Rhodia, decamethylcyclo-pentasiloxane, sold under the name of "Volatile Silicone 7158" by Union Carbide or "Silbione 70045 V 5" by Rhodia, and their mixtures.

Mention may also be made of cyclocopolymers of the dimethylsiloxane/methylalkylsiloxane type, such as "Silicone Volatile FZ 3109", sold by Union Carbide, with the chemical structure:

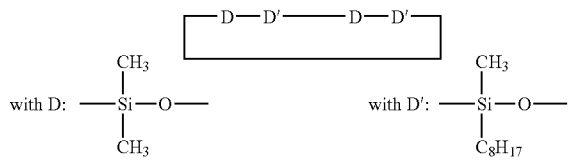

Mention may also be made of mixtures of cyclic silicones with organic compounds derived from silicon, such as the mixture of octamethylcyclotetra-siloxane and of tetratrimethylsilylpentaerythritol (50/50) and the mixture of octamethylcyclotetrasiloxane and of oxy-1,1'-[2,2,2',2',3,3'-hexa(trimethyl-silyloxy)]bisneopentane;

(ii) linear volatile silicones having 2 to 9 silicon atoms and having a viscosity of less than or equal to $5.10^{-6}$ m$^2$/s at 25° C. It is, for example, decamethyltetrasiloxane, sold in particular under the name "SH 200" by Toray Silicone. Silicones coming within this class are also described in the article published in Cosmetics and Toiletries, Vol. 91, January 76, p. 27–32, Todd & Byers, "Volatile Silicone Fluids for Cosmetics".

Mention may in particular be made, among nonvolatile silicones, of polyalkylsiloxanes, polyarylsiloxanes, polyalkylarylsiloxanes, silicone gums and resins, polyorganosiloxanes modified by organofunctional groups, and their mixtures.

The organomodified silicones which can be used in accordance with the invention are silicones as defined above and comprising, in their structure, one or more organofunctional groups attached via a hydrocarbonaceous group.

Mention may be made, among the organomodified silicones, of polyorganosiloxanes comprising:

polyethyleneoxy and/or polypropyleneoxy groups optionally comprising $C_6$–$C_{24}$ alkyl groups, such as the products known as dimethicone copolyol sold by Dow Corning under the name DC 1248 or the Silwet® L 722, L 7500, L 77 and L 711 oils from Union Carbide and the ($C_{12}$) alkyl methicone copolyol sold by Dow Corning under the name Q2 5200;

substituted or unsubstituted amino groups, such as the products sold under the name GP 4 Silicone Fluid and GP 7100 by Genesee or the products sold under the names Q2 8220 and Dow Corning 929 or 939 by Dow Corning. The substituted amino groups are in particular $C_1$–$C_4$ aminoalkyl groups;

thiol groups, such as the products sold under the names "GP 72 A" and "GP 71" from Genesee;

alkoxylated groups, such as the product sold under the name "Silicone Copolymer F-755" by SWS Silicones and Abil Wax® 2428, 2434 and 2440 by Goldschmidt;

hydroxylated groups, such as the polyorganosiloxanes comprising a hydroxyalkyl functional group disclosed in French patent application FR-A-85 16334;

acyloxyalkyl groups, such as, for example, the polyorganosiloxanes disclosed in patent U.S. Pat. No. 4,957,732;

anionic groups of the carboxylic acid type, such as, for example, in the products disclosed in patent EP 186 507 from Chisso Corporation, or of the alkylcarboxylic type, such as those present in the product X-22-3701E from Shin-Etsu; 2-hydroxyalkyl-sulfonate or 2-hydroxyalkyl thiosulfate, such as the products sold by Goldschmidt under the names "Abil® S201" and "Abil® S255";

hydroxyacylamino groups, such as the polyorganosiloxanes disclosed in application EP 342 834. Mention may be made, for example, of the product Q2-8413 from Dow Corning.

The composition according to the invention can comprise one or more mineral, vegetable or animal oils. Mention may in particular be made, as oils of vegetable origin, of sweet almond oil, avocado oil, castor oil, olive oil, jojoba oil, sunflower oil, wheat germ oil, sesame oil, groundnut oil, grape seed oil, soybean oil, rapeseed oil, safflower oil, coconut oil, corn oil, hazelnut oil, karite butter, palm oil, apricot kernel oil or calophyllum oil; as oil of animal origin, of perhydrosqualene; as oils of mineral origin, of liquid paraffin and liquid petrolatum; and of their mixtures.

The composition according to the invention can comprise one or more polyisobutenes and poly(α-olefins) chosen from those well known in the art.

The composition according to the invention can comprise one or more esters. Mention may in particular be made, as examples, of esters of fatty acids, such as isopropyl myristate, isopropyl palmitate, 2-ethylhexyl palmitate, purcellin oil (stearyl octanoate), isononyl isononanoate, isostearyl isononanoate, isopropyl lanolate, and their mixtures.

The composition according to the invention can comprise one or more soluble or dispersed anionic polymers well known per se. The anionic polymers generally used in the present invention are polymers comprising groups derived from carboxylic, sulfonic or phosphoric acids and exhibiting a weight-average molecular mass of between 500 and 5 000 000.

The carboxyl groups are contributed by unsaturated carboxylic monoacid or diacid monomers, such as those corresponding to the formula:

in which n is an integer from 0 to 10, A denotes a methylene group, optionally connected to the carbon atom of the unsaturated group or to the neighboring methylene group when n is greater than 1 via a heteroatom, such as oxygen or sulfur, $R_1$ denotes a hydrogen atom or a phenyl or benzyl group, $R_2$ denotes a hydrogen atom or a lower alkyl or carboxyl group, and $R_3$ denotes a hydrogen atom, a lower alkyl group or a —$CH_2$—COOH, phenyl or benzyl group.

In the above formula (XII), a lower alkyl group preferably comprises from 1 to 4 carbon atoms and denotes in particular the methyl and ethyl groups.

The preferred anionic polymers comprising carboxyl groups according to the invention are:

A) Homo- or copolymers of acrylic or methacrylic acid or their salts and in particular the products sold under the names Versicol® E or K by Allied Colloid or Ultrahold® by BASF, the copolymers of acrylic acid and of acrylamide sold in the form of their sodium salt under the names Reten® 421, 423 or 425 by Hercules or the sodium salts of polyhydroxycarboxylic acids.

B) Copolymers of acrylic acid or methacrylic acid with a monoethylenic monomer, such as ethylene, styrene, vinyl esters or esters of acrylic or methacrylic acid, optionally grafted onto a polyalkylene glycol, such as polyethylene glycol, and optionally crosslinked. Such polymers are disclosed in particular in French patent 1 222 944 and German application 2 330 956, the copolymers of this type comprising, in their chain, an optionally N-alkylated and/or -hydroxyalkylated acrylamide unit, such as disclosed in particular in Luxembourgian patent applications 75370 and 75371 or provided under the name Quadramer® by American Cyanamid. Mention may also be made of copolymers of acrylic acid and of $C_1$–$C_4$ alkyl methacrylate and the copolymer of methacrylic acid and of ethyl acrylate sold under the name Luvimer® MAEX by BASF.

C) Copolymers derived from crotonic acid, such as those comprising, in their chain, vinyl acetate or propionate units and optionally other monomers, such as allyl or methallyl ester, vinyl ether or vinyl ester of a linear or branched saturated carboxylic acid comprising a long hydrocarbonaceous chain, such as those comprising at least 5 carbon atoms, it optionally being possible for these polymers to be grafted and crosslinked, or alternatively a vinyl, allyl or methallyl ester of a . or .-cyclic carboxylic acid. Such polymers are disclosed, inter alia, in French patents numbers 1 222 944, 1 580 545, 2 265 782, 2 265 781, 1 564 110 and 2 439 798. Commercial products coming within this class are the Resins 28-29-30, 26-13-14 and 28-13-10 sold by National Starch.

D) Polymers derived from maleic, fumaric or itaconic acids or anhydrides with vinyl esters, vinyl ethers, vinyl halides, phenylvinyl derivatives, or acrylic acid and its esters; these polymers can be esterified. Such polymers are disclosed in particular in patents U.S. Pat. Nos. 2,047,398, 2,723,248 and 2,102,113 and patent GB 839 805 and in particular those sold under the names Gantrez® AN or ES by ISP.

Polymers also coming within this class are copolymers of maleic, citraconic or itaconic anhydrides and of an allyl or methallyl ester, optionally comprising an acrylamide or methacrylamide group, an α-olefin, acrylic or methacrylic esters, acrylic or methacrylic acids, or vinylpyrrolidone in their chain; the anhydride functional groups are monoesterified or monoamidated. These polymers are, for example, disclosed in French patents 2 350 384 and 2 357 241 of the Applicant Company.

E) Polyacrylamides comprising carboxylate groups.

The polymers comprising sulfo groups are polymers comprising vinylsulfonic, styrenesulfonic, naphthalenesulfonic or acrylamidoalkylsulfonic units.

These polymers can in particular be chosen from:

salts of polyvinylsulfonic acid having a molecular mass of between approximately 1000 and 100 000, as well as copolymers with an unsaturated comonomer, such as acrylic or methacrylic acids and their esters, as well as acrylamide or its derivatives, vinyl ethers and vinylpyrrolidone;

salts of polystyrenesulfonic acid, the sodium salts having a molecular mass of approximately 500 000 and of approximately 100 000 sold respectively under the names Flexan® 500 and Flexan® 130 by National Starch. These compounds are disclosed in patent FR 2 198 719;

salts of polyacrylamidesulfonic acids, such as those mentioned in patent U.S. Pat. No. 4,128,631 and more particularly the polyacrylamidoethylpropanesulfonic acid sold under the name Cosmedia Polymer® HSP 1180 by Henkel.

According to the invention, the anionic polymers are preferably chosen from acrylic acid copolymers, such as the acrylic acid/ethyl acrylate/N-tert-butylacrylamide terpolymer sold under the name Ultrahold Strong® by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by National Starch, polymers derived from maleic, fumaric or itaconic acids or anhydrides with vinyl esters, vinyl ethers, vinyl halides, phenylvinyl derivatives, or acrylic acid and its esters, such as the monoesterified methyl vinyl ether/maleic anhydride copolymer sold under the name Gantrez® ES 425 by ISP, copolymers of methacrylic acid and of methyl methacrylate sold under the name Eudragit® L by Rohm Pharma, the copolymer of methacrylic acid and of ethyl acrylate sold under the name Luvimer® MAEX by BASF, the vinyl acetate/crotonic acid copolymer sold under the name Luviset® CA 66 by BASF and the vinyl acetate/crotonic acid/polyethylene glycol terpolymer [lacuna] under the name Aristoflex® A by BASF.

The most particularly preferred anionic polymers are chosen from the monoesterified methyl vinyl ether/maleic anhydride copolymer sold under the name Gantrez® ES 425 by ISP, the copolymers of methacrylic acid and of methyl methacrylate sold under the name Eudragit® L by Rohm Pharma, the copolymer of methacrylic acid and of ethyl acrylate sold under the name Luvimer® MAEX by BASF or the vinylpyrrolidone/acrylic acid/lauryl methacrylate terpolymer sold under the name Acrylidone® LM by ISP.

According to the invention, the anionic polymers can also be used in the latex or pseudolatex form, that is to say in the form of an aqueous dispersion of insoluble polymer particles.

According to the invention, the anionic polymer(s) can represent from 0.1% to 20% by weight, preferably from 0.2% to 15% by weight and more preferably still from 0.5% to 10% by weight, of the total weight of the final composition.

The composition according to the invention can comprise one or more soluble or dispersed nonionic polymers. Mention may in particular be made, as nonionic polymers which can be used according to the invention, of:

vinylpyrrolidone homopolymers;

copolymers of vinylpyrrolidone and of vinyl acetate;

polyalkyloxazolines, such as the polyethyloxazolines provided by Dow Chemical under the names PEOX® 50 000, PEOX® 200 000 and PEOX® 500 000;

vinyl acetate homopolymers, such as the product provided under the name Appretan® EM by Hoechst or the product provided under the name Rhodopas® A 012 by Rhône-Poulenc;

copolymers of vinyl acetate and of acrylic ester, such as the product provided under the name Rhodopas® AD 310 from Rhône-Poulenc;

copolymers of vinyl acetate and of ethylene, such as the product provided under the name Appretan® TV by Hoechst;

copolymers of vinyl acetate and of maleic ester, for example of dibutyl maleate, such as the product provided under the name Appretan® MB Extra by Hoechst;

copolymers of polyethylene and of maleic anhydride;

alkyl acrylate homopolymers and alkyl methacrylate homopolymers, such as the product provided under the name Micropearl® RQ 750 by Matsumoto or the product provided under the name Luhydran® A 848 S by BASF;

acrylic ester copolymers, such as, for example, copolymers of alkyl acrylates and of alkyl methacrylates, such as the products provided by Rohm & Haas under the names Primal® AC-261 K and Eudragit® NE 30 D, by BASF under the names Acronal® 601, Luhydran® LR 8833 or 8845, or by Hoechst under the names Appretan® N 9213 or N9212;

copolymers of acrylonitrile and of a nonionic monomer chosen, for example, from butadiene and alkyl (meth) acrylates; mention may be made of the products provided under the names Nipol® LX 531 8 by Nippon Zeon or those provided under the name CJ 0601 8 by Rohm & Haas;

polyurethanes, such as the products provided under the names Acrysol® RM 1020 or Acrysol® RM 2020 by Rohm & Haas or the products Uraflex® XP 401 UZ or Uraflex® XP 402 UZ [lacuna] by DSM Resins;

copolymers of alkyl acetate and of urethane, such as the product 8538-33 [lacuna] by National Starch;

polyamides, such as the product Estapor® LO 11 provided by Rhône-Poulenc.

The alkyl groups of the nonionic polymers preferably comprise from 1 to 6 carbon atoms.

The composition for the treatment of keratinous substances according to the invention can comprise one or more of the beneficial agents for keratinous substances described above in a total amount ranging from 0.001% to 20% by weight, preferably from 0.01% to 10% by weight and more particularly from 0.1 to 5% by weight, with respect to the total weight of the composition.

The compositions of the invention in addition advantageously comprise at least one surface-active agent which is generally present in an amount of between 0.05% and 50% by weight approximately, preferably between 0.1% and 40% and more preferably still between 0.55% and 30%, with respect to the total weight of the composition.

This surface-active agent can be chosen from anionic, amphoteric, nonionic or cationic surface-active agents or their mixtures.

The surfactants which are suitable for implementing the present invention are in particular the following:

(i) Anionic Surfactant(s)

Their nature does not assume a truly critical character within the context of the present invention.

Thus, mention may in particular be made, by way of example of anionic surfactants which can be used, alone or [lacuna] mixtures, in the context of the present invention, of (nonlimiting list) the salts (in particular alkali metal, especially sodium, salts, ammonium salts, amine salts, aminoalcohol salts or magnesium salts) of the following compounds: alkyl sulfates, alkyl ether sulfates, alkylamido ether sulfates, alkylarylpolyether sulfates, monoglyceride sulfates; alkylsulfonates, alkyl phosphates, alkylamidesulfonates, alkylarylsulfonates, α-olefinsulfonates, paraffinsulfonates; alkyl sulfosuccinates, alkyl ether sulfosuccinates, alkylamidesulfosuccinates; alkyl sulfosuccinamates; alkyl sulfoacetates; alkyl ether phosphates; acylsarcosinates; acylisethionates and N-acyltaurates, the alkyl or acyl radical of all these different compounds preferably comprising from 8 to 24 carbon atoms, and the aryl radical preferably denoting a phenyl or benzyl group. Mention may also be made, among the anionic surfactants which can also be used, of the salts of fatty acids, such as the salts of oleic, ricinoleic, palmitic and stearic acids, the acids of coconut oil or of hydrogenated coconut oil, and acyllactylates in which the acyl radical comprises 8 to 20 carbon atoms. Use may also be made of weakly anionic surfactants, such as alkyl-D-galactosideuronic acids and their salts, as well as the polyoxyalkylenated ($C_6$–$C_{24}$)alkyl ether carboxylic acids, the polyoxyalkylenated ($C_6$–$C_{24}$)alkylaryl ether carboxylic acids, the polyoxyalkylenated ($C_6$–$C_{24}$) alkylamido ether carboxylic acids and their salts, in particular those comprising from 2 to 50 ethylene oxide groups, and their mixtures.

Among the anionic surfactants, it is preferable to use, according to the invention, alkyl sulfate and alkyl ether sulfate salts and their mixtures.

(ii) Nonionic Surfactant(s):

The nonionic surface-active agents themselves are also compounds which are well known per se (in this respect see in particular the "Handbook of Surfactants" by M. R. Porter, published by Blackie & Son (Glasgow and London), 1991, pp. 116–178) and, in the context of the present invention, their nature does not assume a critical character. They can thus be chosen especially from (nonlimiting list) polyethoxylated, polypropoxylated or polyglycerolated fatty alcohols, α-diols, alkylphenols or acids which have a fatty chain comprising, for example, 8 to 18 carbon atoms, it being possible for the number of ethylene oxide or propylene oxide groups to range especially from 2 to 50 and it being possible for the number of glycerol groups to range especially from 2 to 30. Mention may also be made of the copolymers of ethylene and propylene oxide and the condensates of ethylene and propylene oxide with fatty alcohols; the polyethoxylated fatty amides preferably having from 2 to 30 mol of ethylene oxide, the polyglycerolated fatty amides on average comprising 1 to 5 glycerol groups and in particular 1.5 to 4; the polyethoxylated fatty amines preferably having 2 to 30 mol of ethylene oxide; the oxyethylenated esters of sorbitan fatty acids having from 2 to 30 mol of ethylene oxide; the sucrose esters of fatty acids, the polyethylene glycol esters of fatty acids, alkylpolyglycosides, the N-alkylglucamine derivatives, or amine oxides, such as the oxides of ($C_{10}$–$C_{14}$)alkylamines or the N-acylaminopropylmorpholine oxides. It should be noted that alkylpolyglycosides constitute nonionic surfactants which come particularly well within the scope of the present invention.

(iii) Amphoteric Surfactant(s):

The amphoteric surface-active agents, the nature of which does not assume a critical character in the context of the present invention, may be especially (nonlimiting list) derivatives of aliphatic secondary or tertiary amines in which the aliphatic radical is a linear or branched chain comprising 8 to 22 carbon atoms and comprising at least one water-solubilizing anionic group (for example carboxylate, sulfonate, sulfate, phosphate or phosphonate); mention may also be made of ($C_8$–$C_{20}$)alkylbetaines, sulfobetaines, ($C_8$–$C_{20}$)alkylamido ($C_1$–$C_6$) alkylbetaines or ($C_8$–$C_{20}$) alkylamido ($C_1$–$C_6$) alkylsulfobetaines.

Mention may be made, among the amine derivatives, of the products sold under the name Miranol, as disclosed in patents U.S. Pat. No. 2,528,378 and U.S. Pat. No. 2,781,354 and with structures:

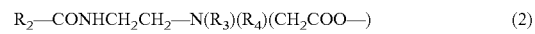

$$R_2\text{—CONHCH}_2\text{CH}_2\text{—N}(R_3)(R_4)(\text{CH}_2\text{COO—}) \qquad (2)$$

in which: $R_2$ denotes an alkyl radical derived from an acid $R_2$—COOH present in hydrolyzed coconut oil, a heptyl, nonyl or undecyl radical, $R_3$ denotes a β-hydroxyethyl group and $R_4$ a carboxymethyl group; and

$$R_5\text{—CONHCH}_2\text{CH}_2\text{—N}(B)(C) \qquad (3)$$

in which:

B represents —CH$_2$CH$_2$OX', C represents —(CH$_2$)$_x$—Y', with z =1 or 2,

X' denotes the —CH$_2$CH$_2$—COOH group or a hydrogen atom

Y' denotes —COOH or the radical —CH$_2$—CHOH—SO$_3$H

R$_5$ denotes an alkyl radical of an acid R$_9$—COOH present in coconut oil or in hydrolyzed linseed oil, an alkyl radical, in particular C$_7$, C$_9$, C$_{11}$ or C$_{13}$, a C$_{17}$ alkyl radical and its iso form or an unsaturated radical C$_{17}$.

These compounds are classified in the CTFA dictionary, 5th Edition, 1993, under the names Disodium Cocoamphodiacetate, Disodium Lauroamphodiacetate, Disodium Caprylamphodiacetate, Disodium Caproamphodiacetate, Disodium Cocoamphodipropionate, Disodium Lauroamphodipropionate, Disodium Caprylamphodipropionate, Disodium Caproamphodipropionate, Lauroamphodipropionic acid and Cocoamphodipropionic acid.

Mention may be made, by way of example, of the cocoamphodiacetate sold under the trade name Miranol C2M concentrate by Rhône-Poulenc.

(iv) The cationic surfactants can be chosen from:

A)—the quaternary ammonium salts of the following general formula (IV):

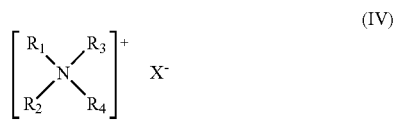

in which X is an anion chosen from the group of the halides (chloride, bromide or iodide) or (C$_2$–C$_6$)alkyl sulfates, more particularly methyl sulfate, of the phosphates, of the alkyl- or alkylarylsulfonates, and of the anions derived from an organic acid, such as acetate or lactate, and a) the R$_1$ to R$_3$ radicals, which can be identical or different, represent a linear or branched aliphatic radical comprising from 1 to 4 carbon atoms or an aromatic radical, such as aryl or alkylaryl. The aliphatic radicals can comprise heteroatoms, such as, in particular, oxygen, nitrogen, sulfur or halogens. The aliphatic radicals are, for example, chosen from alkyl, alkoxy or alkylamide radicals, R$_4$ denotes a linear or branched alkyl radical comprising from 16 to 30 carbon atoms.

Preferably, the cationic surfactant is a behenyltrimethylammonium salt (for example chloride).

b) the R$_1$ and R$_2$ radicals, which can be identical or different, represent a linear or branched aliphatic radical comprising from 1 to 4 carbon atoms or an aromatic radical, such as aryl or alkylaryl. The aliphatic radicals can comprise heteroatoms, such as, in particular, oxygen, nitrogen, sulfur or halogens. The aliphatic radicals are, for example, chosen from alkyl, alkoxy, alkylamide and hydroxyalkyl radicals comprising approximately from 1 to 4 carbon atoms;

R$_3$ and R$_4$, which are identical or different, denote a linear or branched alkyl radical comprising from 12 to 30 carbon atoms, said radical comprising at least one ester or amide functional group. R$_3$ and R$_4$ are chosen in particular from (C$_{12}$–C$_{22}$)alkylamido(C$_2$–C$_6$)alkyl or (C$_{12}$–C$_{22}$)alkyl acetate radicals.

Preferably, the cationic surfactant is a stearamidopropyldimethyl(myristyl acetate)ammonium salt (for example chloride).

B)—imidazolinium quaternary ammonium salts, such as, for example, that of following formula (V):

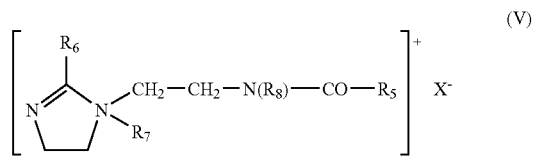

in which R$_5$ represents an alkenyl or alkyl radical comprising from 8 to 30 carbon atoms, for example derivatives of tallow fatty acids, R$_6$ represents a hydrogen atom, a C$_1$–C$_4$ alkyl radical or an alkenyl or alkyl radical comprising from 8 to 30 carbon atoms, R$_7$ represents a C$_1$–C$_4$ alkyl radical, R$_8$ represents a hydrogen atom or a C$_1$–C$_4$ alkyl radical and X is an anion chosen from the group of the halides, phosphates, acetates, lactates, alkyl sulfates, or alkyl- or alkylarylsulfonates. R$_5$ and R$_6$ preferably denote a mixture of alkenyl or alkyl radicals comprising from 12 to 21 carbon atoms, for example derivatives of tallow fatty acids, R$_7$ preferably denotes methyl and R$_8$ preferably denotes hydrogen. Such a product is, for example, Quaternium-27 (CTFA 1997) or Quaternium-83 (CTFA 1997), which are sold under the names "Rewoquat" W 75, W90, W75PG or W75HPG by Witco, C)—quaternary diammonium salts of formula (VI):

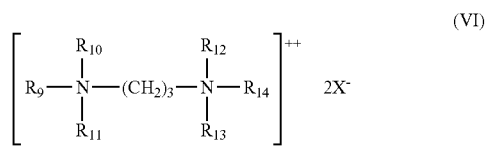

in which R$_9$ denotes an aliphatic radical comprising approximately from 16 to 30 carbon atoms, R$_{10}$, R$_{11}$, R$_{12}$, R$_{13}$ and R$_{14}$, which are identical or different, are chosen from hydrogen or an alkyl radical comprising from 1 to 4 carbon atoms and X is an anion chosen from the group of the halides, acetates, phosphates, nitrates and methyl sulfates. Such quaternary diammonium salts comprise in particular propanetallowdiammonium dichloride, D)—quaternary ammonium salts comprising at least one ester functional group of following formula (VII):

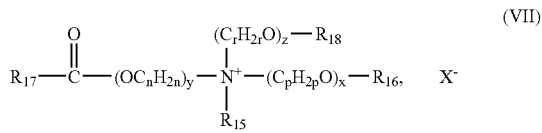

in which:

R$_{15}$ is chosen from C$_1$–C$_6$ alkyl radicals and C$_1$–C$_6$ hydroxyalkyl or dihydroxyalkyl radicals;

$R_{16}$ is chosen from:
the

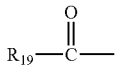

radical
saturated or unsaturated, linear or branched, $C_1$–$C_{22}$ hydrocarbonaceous radicals $R_{20}$,
the hydrogen atom,
$R_{18}$ is chosen from:
the

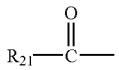

radical
saturated or unsaturated, linear or branched, $C_1$–$C_6$ hydrocarbonaceous radicals $R_{22}$,
the hydrogen atom,
$R_{17}$, $R_{19}$ and $R_{21}$, which are identical or different, are chosen from saturated or unsaturated, linear or branched, $C_7$–$C_{21}$ hydrocarbonaceous radicals;
n, p and r, which are identical or different, are integers having values from 2 to 6;
y is an integer having a value from 1 to 10;
x and z, which are identical or different, are integers having values from 0 to 10;
$X^-$ is an organic or inorganic, simple or complex anion;
with the proviso that the sum x+y+z has a value from 1 to 15, that when x has a value of 0, then $R_{16}$ denotes $R_{20}$, and that when z has a value of 0, then $R_{18}$ denotes $R_{22}$.

Use is more particularly made of the ammonium salts of formula (VII) in which:
$R_{15}$ denotes a methyl or ethyl radical,
x and y are equal to 1;
z is equal to 0 or 1;
n, p and r are equal to 2;
$R_{16}$ is chosen from:
the

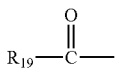

radical
methyl, ethyl or $C_{14}$–$C_{22}$ hydrocarbonaceous radicals
the hydrogen atom;
$R_{17}$, $R_{19}$ and $R_{21}$, which are identical or different, are chosen from saturated or unsaturated, linear or branched, $C_7$-$C_{21}$ hydrocarbonaceous radicals;
$R_{18}$ is chosen from:
the

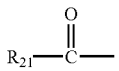

radical
the hydrogen atom.

Such compounds are, for example, sold under the names Dehyquart by Henkel, Stepanquat by Stepan, Noxamium by Ceca or Rewoquat WE 18 by Rewo-Witco.

Preference is given, among quaternary ammonium salts, to behenyltrimethylammonium chloride, stearamidopropyldimethyl(myristyl acetate)ammonium chloride, sold under the name "Ceraphyl 70" by Van Dyk, or Quaternium-27 or Quaternium-83, which are sold by Witco.

Use may be made, in the compositions according to the invention, of mixtures of surface-active agents and in particular of mixtures of anionic surface-active agents, of mixtures of anionic surface-active agents and of amphoteric, cationic or nonionic surface-active agents, or of mixtures of cationic surface-active agents with nonionic or amphoteric surface-active agents. A particularly preferred mixture is a mixture composed of at least one anionic surface-active agent and of at least one amphoteric surface-active agent.

The composition of the invention can also comprise at least one additive chosen from associative or nonassociative, anionic, amphoteric, zwitterionic, nonionic or cationic, natural or synthetic polymeric thickeners, nonpolymeric thickeners, such as acids or electrolytes, fragrances, pearlescent agents, preservatives, colorants, pH agents, inorganic or organic particles, vitamins, provitamins, panthenol and any other additive conventionally used in the cosmetic field which does not affect the properties of the compositions according to the invention.

These additives are present in the composition according to the invention in proportions which can range from 0 to 40% by weight with respect to the total weight of the composition. The precise amount of each additive is easily determined by a person skilled in the art according to its nature and its function.

The compositions according to the invention can be detergent compositions, such as shampoos, shower gels or foam baths. In this embodiment of the invention, the compositions comprise a washing base, generally an aqueous washing base.

The surfactant or surfactants forming the washing base can be chosen without distinction, alone or as mixtures, from the anionic, amphoteric, nonionic and cationic surfactants as defined above.

Use is preferably made of an anionic surface-active agent chosen from sodium, triethanolamine or ammonium ($C_{12}$–$C_{14}$)alkyl sulfates, sodium, triethanolamine or ammonium ($C_{12}$–$C_{14}$)alkyl ether sulfates oxyethylenated with 2.2 mol of ethylene oxide, sodium cocoyl isethionate and sodium α-($C_{14}$–$C_{16}$)olefinsulfonate and their mixture with:
either an amphoteric surface-active agent, such as the amine derivatives named disodium cocoamphodipropionate or sodium cocoamphopropionate sold in particular by Rhône-Poulenc under the trade name "Miranol C2M Conc" as an aqueous solution comprising 38% of active material or under the name Miranol C32;
or an amphoteric surface-active agent of zwitterionic type, such as alkyl betaines, in particular the coco betaine sold under the name "Dehyton AB 30" by Henkel as an aqueous solution comprising 32% of AM.

The amount and the quality of the washing base are those sufficient to confer a satisfactory foaming and/or detergent power on the final composition.

Thus, according to the invention, the washing base can represent from 4% to 50% by weight, preferably from 6% to 35% by weight and more preferably still from 8% to 25% by weight, of the total weight of the final composition.

A further subject matter of the invention is a process for the treatment of keratinous substances, such as the skin or hair, characterized in that it consists in applying, to the keratinous substances, a cosmetic composition as defined above and in then optionally rinsing with water.

Thus, this process according to the invention makes it possible to retain the form of the hairstyle or to treat, care for or wash or remove make-up from the skin, hair or any other keratinous substance.

The compositions of the invention can also be provided in the form of a rinse-out or leave-in conditioner or of permanent-wave, hair-straightening, dyeing or bleaching compositions or alternatively in the form of rinse-out compositions, to be applied before or after a dyeing, a bleaching, a permanent wave or a hair straightening or alternatively between the two stages of a permanent wave or a hair straightening.

When the composition is provided in the form of an optionally rinse-out conditioner, it advantageously comprises at least one cationic surfactant, its concentration generally of between 0.1 and 10% by weight and preferably of 0.5 to 5% by weight with respect to the total weight of the composition.

The compositions of the invention can also be provided in the form of washing compositions for the skin and in particular in the form of solutions or gels for the bath or shower or of make-up-removing products.

The compositions according to the invention can also be provided in the form of aqueous or aqueous/alcoholic lotions for caring for the skin and/or hair.

The cosmetic compositions according to the invention can be provided in the gel, milk, cream, emulsion, thickened lotion or foam form and can be used for the skin, nails, eyelashes, lips and more particularly the hair.

The compositions can be packaged in various forms, in particular in vaporizers, pump-action sprays or in aerosol containers, in order to provide for application of the composition in the vaporized form or in the foam form. Such packaging forms are indicated, for example, when it is desired to obtain a spray, a lacquer or a foam for hair treatment.

In all which follows or which precedes, the percentages expressed are by weight.

The invention will now be more completely illustrated using the following examples, which should not be regarded as limiting it to the embodiments described. In the examples, AM means active material.

In the examples, the commercial names have the following definitions:

EXAMPLE 1

A conditioner in accordance with the invention was prepared with the following composition:

| | |
|---|---|
| Inulin (Raftiline HP from Orafti) | 10.6 g AM |
| Behenyltrimethylammonium chloride | 4 g AM |
| Highly esterified lemon pectin (Instant CJ 204 from Herbstreith and Fox) | 1.9 g AMAM |
| Amodimethicone (Belsil ADM 6057 E from Wacker) | 1.7 g AM |
| Water q.s. for | 100 g |

The composition has a thick and very melting texture during the application to wet hair. It has good rinsability. The wetted hair is not rendered heavy and the shaping is easy.

EXAMPLES 2 TO 5

The conditioners in accordance with the invention with the following compositions were prepared:

| | 2 | 3 | 4 | 5 |
|---|---|---|---|---|
| Inulin (Raftiline HP from Orafti) | 12 g AM | 3 g AM | 8 g | 15 g |
| Highly esterified lemon pectin (Instant CJ 204 from Herbstreith and Fox) | — | 3.5 g | — | 0.7 g |
| Xanthan gum | 0.8 g | — | — | — |
| Pregelatinized anionic oxidized potato starch (Prejel PA 5 from Avebe) | — | — | 5 g | — |
| Isopropyl myristate | — | — | 2 g | — |
| Amodimethicone (Belsil ADM 6057 E from Wacker) | — | 2 g | — | 1.5 g |
| Divinyldimethicone/dimethicone crosslinked as cationic emulsion (DC2-1997 from Dow Corning) | 1.7 g | — | — | — |
| Polyquaternium 10 (JR 400 from Amerchol) | — | 1.8 g | — | — |
| Behenyltrimethylammonium chloride | 2 g | — | — | — |
| Palmitylamidopropyltrimethylammonium chloride | — | — | 1.8 g | — |
| Dipalmitoylethylhydroxyethylmethyl ammonium methyl sulfate/cetearyl alcohol | — | — | — | 3.5 g |
| Benzotriazole screening agent derived from heptamethylhydrotrisiloxane (Silatrizole from Rhodia Chimie) | — | 1 g | — | — |
| Water q.s. for | 100 g | 100 g | 100 g | 100 g |

The treated hair has the same properties as that treated with the composition of example 1.

The invention claimed is:

1. A cosmetic composition, comprising, in a cosmetically acceptable medium, at least one fructan, at least one polysaccharide and at least one beneficial agent for keratinous substances, said composition being applicable to keratinous substances;
   wherein said fructan is inulin and is present at a concentration of between 0.01% and 20% by weight with respect to the total weight of said composition; and
   wherein said polysaccharide is selected from glucans, modified or unmodified starches, amylase, amylopectin, glycogen, dextrans, celluloses and their derivatives, mannans, xylans, lignins, arabans, galactans, galacturonans, chitin, chitosans, glucoronoxylans, arabinoxylans, xyloglucans, glucomannans, pectic acids and pectins, alginic acid and alginates, arabinogalactans, carrageenins, agars, glycosaminoglucans, gums Arabic, gums tragacanth, ghatti gums, karaya gums, locust bean gums, galactomannans, xanthan gums, and mixtures thereof and is present at a concentration of between 0.01% and 20% by weight with respect to the total weight of aid composition.

2. The composition of claim 1, wherein said beneficial agent for keratinous substances is selected from:
(1) amino acids, oligopeptides, peptides and proteins, which may be hydrolyzed or modified,
(2) branched or unbranched fatty acids and alcohols,
(3) animal, vegetable or mineral waxes,
(4) ceramides and pseudoceramides,
(5) hydroxylated organic acids,
(6) UV screening agents,
(7) antioxidants and agents for combating free radicals,
(8) chelating agents,
(9) antidandruff agents,
(10) seborrhea-regulating agents,
(11) soothing agents,
(12) cationic surfactants,
(13) amphoteric polymers,
(14) organomodified or non-organomodified silicones,
(15) mineral, vegetable or animal oils,
(16) polyisobutenes and poly($\alpha$-olefins),
(17) esters of fatty acids,
(18) soluble and dispersed anionic polymers,
(19) soluble and dispersed nonionic polymers, and mixtures thereof.

3. The composition of claim 2, wherein said amino acids, are selected from cysteine, lysine, alanine, N-phenylalaflifle, arginine, glycine, leucine, and mixtures thereof.

4. The composition of claim 2, wherein said branched and unbranched fatty acids and alcohols comprise from 8 to 30 carbon atoms and are selected from palmitic acid, oleic acid, linoleic acid, myristic acid, stearic acid, lauric acid, palmityl, oleyl, linoleyl, myristyl, stearyl and lauryl alcohols, and mixtures thereof.

5. The composition of claim 2, wherein said ceramides and pseudoceramides are selected from ceramide classes I, II, III and V according to the Dawning classification, and mixtures thereof.

6. The composition of claim 2, wherein said hydroxylated organic acids are selected from citric acid, lactic acid, tartaric acid, malic acid, and mixtures thereof.

7. The composition of claim 2, wherein said uv screening agents are selected from dibenzoylmethane derivatives, p-aminobenzoic acid and its esters, salicylates, cinnamic acid esters, benzotriazole derivatives, triazine derivatives, $\beta,\beta'$-diphenylacrylate derivatives, 2-phenylbenzimidazo-5-sulfonic acid and its salts, benzophenone derivatives, benzylidenecamphor derivatives, silicone screening agents, and mixtures thereof.

8. The composition of claim 2, wherein said antioxidants and the agents for combating free radicals are selected from ascorbic acid, ascorbylated compounds, t-butylhydroquinone, polyphenols, sodium sulfite, erythorbic acid, flavonoids, and mixtures thereof.

9. The composition of claim 2, wherein said chelating agents are selected from EDTA and its salts, phosphate-comprising compounds, phosphonic acids and their salts, and mixtures thereof.

10. The composition of claim 2, wherein said antidandruff agents are selected from:
benzethonium chloride, benzalkonium chloride, chlorhexidine, chloramine-T, chloramine-B, 1,3-dibromo-5,5-dimethylhydantoin, 1,3-dichloro-5,5-dimethylhydantoin, 3-bromo-l-chloro-5,5-dimethyihydantoin or N-chlorosuccinimide;
1-hydroxy-2-pyridone derivatives;
trihalocarbamides;
triclosan;
azole-comprising compounds;
antifungal polymers;
selenium sulfides;
sulfur in various forms;
and mixtures thereof.

11. The composition of claim 2, wherein said seborrhea-regulating agents are selected from succinylchitosan, poly-$\beta$-alanine, and mixtures thereof.

12. The composition of claim 2, wherein said soothing agents are selected from azulene, glycyrrhetinic acid, and mixtures thereof.

13. The composition of claim 2, wherein said cationic surfactants are selected from salts of primary, secondary and tertiary fatty amines, quaternary ammonium salts, imidazoline derivatives, amine oxides with a cationic nature, and mixtures thereof.

14. The composition of claim 2, wherein said silicones, are selected from volatile silicones, nonvolatile silicones, polyorgano-siloxanes modified by organofunctional groups, and mixtures thereof.

15. The composition of claim 2, wherein said esters of fatty acids are selected from isopropyl myristate, isopropyl palmitate, 2-ethylhexyl palmitate, purcellin oil, isononyl isononanoate, isostearyl isononanoate, isopropyl lanolate, and mixtures thereof.

16. The composition of claim 2, wherein said soluble and dispersed anionic polymers are selected from polymers comprising groups derived from carboxylic, sulfonic or phosphoric acids that exhibit a weight-average molecular mass of between 500 and 5,000,000; and mixtures thereof.

17. The composition of claim 2, wherein said soluble and dispersed nonionic polymers are selected from vinylpyrrolidone homopolymers; copolymers of vinylpyrrolidone and of vinyl acetate; polyalkyloxazolines; vinyl acetate homopolymers; copolymers of vinyl acetate and of acrylic ester; copolymers of vinyl acetate and of ethylene; copolymers of vinyl acetate and of maleic ester; copolymers of polyethylene and of maleic anhydride; alkyl acrylate homopolymers; alkyl methacrylate homopolymers; acrylic ester copolymers; copolymers of acrylonitrile and of butadiene or of alkyl (meth)acrylate; polyurethanes; copolymers of alkyl acetate and of urethane; polyamides; and mixtures thereof.

18. The composition of claim 1, wherein said the beneficial agent is present at a concentration of between 0.001% and 20% by weight with respect to the total weight of said composition.

19. The composition of claim 1, further comprising at least one surface-active agent selected from anionic, cationic, nonionic and amphoteric surfactants and mixtures thereof.

20. The composition of claim 19, wherein said surface-active agent is present at a concentration of between 0.1% and 50% by weight with respect to the total weight of the composition.

21. The composition of any one of claims 1, 2, and 18, wherein said composition is a shampoo, conditioner, composition for perming hair, for straightening hair, for dyeing hair, for bleaching hair, a rinse-out composition to be applied between stages of a permanent wave or hair straightening, or a washing composition for a body.

22. A process for the treatment of keratinous substances comprising the steps of applying to said keratinous substances, a cosmetic composition according to claim 1.

23. The process of claim 22, further comprising the step of rinsing said keratinous substances with water.

24. The composition of claim 1, wherein said galactomannans are guar gums and nonionic derivatives thereof.

25. The composition of claim 24, wherein said nonionic derivative is hydroxyipropyl guar.

26. The composition of claim 2, wherein said animal waxes are selected from beeswax, spermaceti, lanolin wax, lanolin derivatives, and mixtures thereof.

27. The composition of claim 2, wherein said vegetable waxes are selected from carnauba wax, candelilla wax, ouricury wax, Japan wax, cocoa butter, cork fiber, sugarcane wax, and mixtures thereof.

28. The composition of claim 2, wherein said animal waxes are selected from paraffin wax, petrolatum wax, lignite wax, microcrystalline waxes, ozokerites, and mixtures thereof.

29. The composition of claim 13, wherein said secondary and tertiary fatty amines are polyoxyakylenated.

30. The composition of claim 13, wherein said quaternary ammonium salts are selected from tetralkylammonium, alkylamidoalkyltrialkylammonium, trialkylbenzylammonium, trialkylhydroxyalkylammonium, alkylpyridinium chlorides and alkylpyridinium bromides.

31. The composition of claim 2 wherein said silicones are organomodified.

32. The composition of claim 2, wherein said silicones are not organomodified.

33. The composition of claim 2, wherein said silicones are soluble in said composition.

34. The composition of claim 2, wherein said silicones are insoluble in said composition.

35. The composition of claim 14, wherein said volatile silicones are cyclic silicones comprising from 3 to 7 silicon atoms.

36. The composition of claim 14, wherein said nonvolatile silicones are selected from polyalkylsiloxanes, polyarylsiloxanes, polyalkylarylsiloxanes, silicone gums and resins.

37. The composition of claim 14, wherein said organofunctional groups are selected from polyethyleneoxy groups, propyleneoxy groups, substituted and unsubstituted amino groups, thiol, alkoxylated groups, hydroxylated groups, acyloxyalky acid groups, carboxylic acid groups, and hydroxyacylamino groups.

38. The composition of claim 2, wherein said mineral oils are selected from liquid paraffin, liquid petrolatum, and mixtures thereof.

39. The composition of claim 2, wherein said vegetable oils are selected from sweet almond oil, avocado oil, castor oil, olive oil, jojoba oil, sunflower oil, wheat germ oil, sesame oil, groundnut oil, grape seed oil, soybean oil, rapeseed seed oil, safflower oil, coconut oil, corn oil, hazelnut oil, karite butter, palm oil, apricot kernel oil, calophyllum oil, and mixtures thereof.

40. The composition according to claim 2, wherein said animal oils are perhydrosqualines and mixtures thereof.

41. The composition of claim 15, wherein said purcellin oil is stearyloctanoate.

42. The composition of claim 1, wherein said fructan is present at a concentration between 0.05% and 10% by weight of said composition.

43. The composition of claim 1, wherein said polysaccharide is present at a concentration of between 0.05% and 10% by weight of said composition.

44. The composition of claim 18, wherein said beneficial agent is present at a concentration of between 0.01% and 10% by weight of said composition.

45. The composition of claim 20, wherein said surface-active agent is present at a concentration of between 0.1% and 40% by weight with respect to the total weight of said composition.

46. The composition of claim 45, wherein said surface-active agent is present at a concentration of between 0.5% and 30% by weight with respect to the total weight of said composition.

47. A composition, comprising, in a cosmetically acceptable medium, at least one fructan, at least one polysaccharide, at least one beneficial agent for keratinous substances, and a cationic surfactant;
wherein said composition is for treating keratinous substances.

48. A detergent composition, comprising, in a cosmetically acceptable medium, at least one fructan, at least one polysaccharide, at least one beneficial agent for keratinous substances, and an aqueous washing base;
wherein said composition is for the treating keratinous substances;
wherein said aqueous washing base is selected from anionic, amphoteric, nonionic, or cationic surfactants, or mixtures thereof; and
wherein said aqueous washing base represents 4% to 50% by weight of the total weight of said composition.

49. A process for the treatment of keratinous substances comprising the steps of applying to said keratinous substances, a cosmetic composition according to claim 21.

* * * * *

UNITED STATES PATENT AND TRADEMARK OFFICE
CERTIFICATE OF CORRECTION

PATENT NO. : 7,151,079 B2  Page 1 of 1
APPLICATION NO. : 10/250896
DATED : December 19, 2006
INVENTOR(S) : Géraldine Fack, Chrystel Pourille-Grethen and Serge Restle It is certified that error appears in the above-identified patent and that said Letters Patent is hereby corrected as shown below:

Column 1, line 36, after "say" insert --,--.
Column 1, line 67, after "[lacuna]" insert --or--.
Column 2, line 18, after "say" insert --,--.
Column 2, line 30, delete "is" and insert therefor --are--
Column 13, line 35, delete "Pat. Nos.".
Column 13, line 67, delete "Pat. No.".
Column 14, line 23, after "[lacuna]" insert --sold--.
Column 14, line 35, after "say" insert --,--.
Column 23, line 3, delete "aid" and insert therefor --said--
Column 23, line 27, delete ",".
Column 23, line 28, delete "phenylalaflifle" and inset therefor --phenylalanine--.
Column 23, line 43, "uv" should read --UV--.
Column 23, line 47, "phenylbenzimidazo" should read --phenylbenzimidazole--.
Column 23, line 65, "dimethylihydantoin" should read --dimethylhydantoin--.
Column 24, line 19, delete "," (second occurrence).
Column 25, line 4, "hydroxyipropyl" should read --hydroxylpropyl--.
Column 26, line 33, delete ",".
Column 26, line 37, after "treating" insert --of--.
Column 26, line 46, delete ",".

Signed and Sealed this

First Day of May, 2007

JON W. DUDAS
*Director of the United States Patent and Trademark Office*